United States Patent
Russo et al.

(10) Patent No.: US 6,653,495 B2
(45) Date of Patent: Nov. 25, 2003

(54) PROCESS FOR OBTAINING MIXTURES OF PHOSPHORIC MONO- AND DIESTERS

(75) Inventors: Antonio Russo, Milan (IT); Claudio Tonelli, Milan (IT)

(73) Assignee: Ausimont S.p.A., Milan (IT)

( * ) Notice: Subject to any disclaimer, the term of this patent is extended or adjusted under 35 U.S.C. 154(b) by 16 days.

(21) Appl. No.: 10/050,845

(22) Filed: Jan. 18, 2002

(65) Prior Publication Data

US 2002/0099234 A1 Jul. 25, 2002

(30) Foreign Application Priority Data

Jan. 23, 2001 (IT) ........ MI2001A0114

(51) Int. Cl.⁷ ............ C07F 9/113; C07F 9/173
(52) U.S. Cl. ........................... 558/114
(58) Field of Search ..................... 558/114

(56) References Cited

U.S. PATENT DOCUMENTS

| | | | |
|---|---|---|---|
| 2,242,218 A | 5/1941 | Auer | |
| 3,492,374 A | 1/1970 | Bleu et al. | |
| 3,665,041 A | 5/1972 | Sianesi et al. | |
| 3,715,378 A | 2/1973 | Sianesi et al. | |
| 3,810,874 A | 5/1974 | Mitsch et al. | |
| 3,935,277 A | 1/1976 | Dear et al. | |
| 4,587,063 A | 5/1986 | Kurosaki et al. | 556/146 |
| 4,946,992 A | 8/1990 | Falk et al. | |
| 5,091,550 A | 2/1992 | Falk et al. | |
| 5,132,445 A | 7/1992 | Falk et al. | |
| 5,714,637 A | 2/1998 | Marchionni et al. | |

FOREIGN PATENT DOCUMENTS

| | | |
|---|---|---|
| DE | 24 05 042 | 8/1975 |
| EP | 0 148 482 A2 | 7/1985 |
| EP | 0 239 123 A2 | 9/1987 |

*Primary Examiner*—Joseph K. McKane
*Assistant Examiner*—Rebecca Anderson
(74) *Attorney, Agent, or Firm*—Arent Fox Kintner Plotkin & Kahn PLLC

(57) ABSTRACT

Process for obtaining mixtures of phosphoric mono- and diesters having the formula:

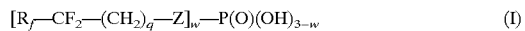

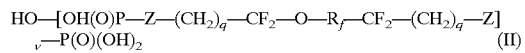

wherein:

$w=1-2$; $v=1-6$; $q=1-20$;

$Z=O(C_2H_4O)_p-$, $O(CH_2)_n-O-$, $O(C_3H_6O)_p-$, $S(C_2H_4O)_p-$, $S(C_3H_6O)_p-$;

$n=1-20$; $p=1-5$;

$R_f$ represents a (per)fluoropolyether chain;

$R_f$ in formula (I) is a monofunctional perfluoropolyether chain wherein the chain end group is selected from: $CF_3O-$, $C_2F_5O-$, $C_3F_7O-$, $Cl(C_3F_6O)-$, $H(C_3F_6O)-$.

8 Claims, No Drawings

PROCESS FOR OBTAINING MIXTURES OF PHOSPHORIC MONO- AND DIESTERS

The present invention relates to a process for obtaining in high yield phosphoric esters having a perfluoropolyoxyalkylene structure useful to give hydro- and oil-repellence in the treatment of various natural and artificial substrata, such as for example, ceramic, wood.

Specifically, the present invention relates to a process which allows to obtain phosphoric esters having a perfluoropolyoxyalkylene structure with high conversions and yields. Besides, the process of the invention allows to obtain, starting from the same precursor alcohol, phosphoric esters having a perfluoropolyoxyalkylene structure with a complete absence of triester groups and to modulate in a predetermined way the molar ratio between monoester and diester groups. Phosphoric esters are therefore obtained having a variable and controllable monoester/diester molar ratio starting from the same precursor alcohol.

It is known that the phosphoric esters of perfluoropolyethers are used to give hydro- and oil-repellence or easy stain removal to a wide range of natural and artificial substrata.

For the above mentioned applications, depending on the type of substratum, mixtures are required having a different content of phosphoric mono- and di-ester to obtain optimal results in connection with the desired effect. Therefore, from the industrial point of view, it would be desirable to have available a process which allows to modulate in a predetermined way the mono/diester composition of the phosphoric esters obtained from the phosphatization reaction.

Phosphoric esters deriving from monofunctional (per)fluoroalkyl alcohols are known in the prior art. These compounds must be phosphoric diesters to confer suitable hydro- and oil-repellence properties. However, the synthesis of diester phosphates in high yield is difficult and it unavoidably leads to a mixture containing significant amounts of triester as by-product. This is undesirable since the phosphoric triester shows adhesion problems to the substratum to which it is desired to confer hydro- and oil-repellence.

Alcoholic precursors have been synthesized having a perfluoroalkyl structure containing two monofunctional perfluorinated chains linked to a hydrogenated alkyl radical having an alcoholic function (di-$R_f$-alcohols wherein $R_f$ is a perfluoroalkyl group) or two alcohol functions (di-$R_f$-diols) as described in U.S. Pat. Nos. 3,935,277 and 4,946,992. Said patents describe the synthesis of di-$R_f$-alcohols and of di-Rf-diols by reaction of $R_f$-ethylenthiols with halogenated alcohols and dials. Phosphoric esters of di-Rf-diols are described in U.S. Pat. Nos. 5,091,550 and 5,132,445. However the synthesis of the precursor alcohols requires many steps and expensive intermediates. The phosphoric esters obtained from said precursors are not easily available on the market.

To impart hydra- and oil-repellence properties to natural and artificial substrata, it is also known, as described in U.S. Pat. No. 3,492,374, the use of phosphates deriving from monofunctional alcohols having a perfluoropolyoxyalkylene structure, of general formula:

[XCF$_2$CF$_2$O(CFXCF$_2$O)$_x$CFXCH$_2$O]$_2$PO(OM)

wherein:

X is F or CF$_3$; x is an integer in the range 1–8; M is a cation such as for example H$^+$, a cation of alkaline metals or an optionally alkyl substituted ammonium ion.

In this patent it is suggested the use of said phosphoric diesters to give oil-repellent properties to various materials for example textile fibres, skin, paper, plastic material, wood, ceramic. However these compounds are not very stable to hydrolysis. Besides, the synthesis reaction is carried out by using POCl$_3$ as phosphating agent: there are no high yields and phosphoric triesters with the above drawbacks are obtained.

The most used method in the prior art for preparing fluorinated phosphoric esters consists in the partial esterification of the phosphor oxychloride POCl$_3$, with an alcohol and subsequent hydrolysis of the reaction intermediates. However this process leads to the formation of phosphoric triesters which give the above drawbacks. Besides, the esterification reaction of alcohols with POCl$_3$ takes place in highly exothermic conditions and with development of hydrochloric acid wherefore severe control measures are required, as regards both the process safety and the material used in the plant construction.

Another phosphatization reaction known in the prior art is the reaction between an alcohol and the phosphoric anhydride P$_2$O$_5$. However this reaction leads to the formation of mixtures of monoesters and diesters in a fixed and not variable ratio, once the starting alcohol has been defined. Therefore this process does not allow to control in a predetermined way the mono/diester composition of the phosphoric esters obtained from the reaction, starting from the same precursor alcohol. From the industrial point of view this is a drawback since mono- and diester mixtures cannot be obtained in a variable ratio starting from the same precursor alcohol.

The need was therefore felt to have available a process for obtaining phosphoric esters having a perfluoropolyoxyalkylene structure (PFPE), which allows to obtain a complete absence of triester groups and to modulate in a predetermined way the molar ratio between the monoester groups —P(O)(OH)$_2$, and the diester groups >PO(OH) present in the final product obtained by the reaction.

The Applicant has surprisingly found a process characterized by high yields and conversions to obtain phosphoric esters having a PFPE structure with the above properties.

An object of the present invention is therefore a process to obtain phosphoric mono- and diesters mixtures having the formula:

[R$_f$—CF$_2$—(CH$_2$)$_q$—Z]$_w$—P(O)(OH)$_{3-w}$     (I)

HO—[OH(O)P—Z—(CH$_2$)$_q$CF$_2$—O—R$_f$CF$_2$—(CH$_2$)$_q$—Z]$_v$—P(O)(OH)$_2$     (II)

wherein:

w=1–2 v=1–6, preferably 1–4;

q=is an integer from 1 to 20, preferably 1–5;

Z=O(C$_2$H$_4$O)$_p$—, O(CH$_2$)$_n$—O—, O(C$_3$H$_6$O)$_p$—, S(C$_2$H$_4$O)$_p$—, S(C$_3$H$_6$O)$_p$—;

n=is an integer from 1 to 20, preferably 1–10;

p=is an integer from 1 to 5, preferably 1–3;

R$_f$ represents a (per)fluoropolyether chain;

R$_f$ in formula (I) is a monofunctional perfluoropolyether chain wherein the chain end group is selected from: CF$_3$O—, C$_2$F$_5$O—, C$_3$—F$_7$O—, Cl(C$_3$F$_6$O)—, H(C$_3$F$_6$O)—;

said process comprising the following steps:

a) a monofunctional alcohol having a perfluoropolyoxyalkylene structure of formula:

R$_f$—CF$_2$—(CH$_2$)$_q$—ZH     (IA)

or a α,ω-diol having a perfluoropolyoxyalkylene structure of formula:

$$HZ-(CH_2)_q-CF_2-O-R_f-CF_2-(CH_2)_q-ZH \quad \text{(IIA)}$$

wherein $R_f$, Z and q have the above meanings, is added with an amount of water in the range 1–60% by moles, preferably 5%–40% by moles, with respect to the alcohol equivalents;

b) the reaction product obtained in step a) is reacted with phosphoric anhydride $P_2O_5$ added in a single portion or in more portions with a ratio between the alcohol equivalents and the moles of phosphoric anhydride in the range 1.5:1–4:1, preferably 2:1–3:1;

c) the compound obtained in step b) is hydrolysed by water or by a diluted solution of hydrochloric acid;

d) optionally the organic phase is separated by a solvent immiscible in water;

e) the product is recovered from the organic phase.

Generally, Rf has a number average molecular weight in the range 300–8,000, preferably 500 and 3,000 and comprises repeating units having at least one of the following structures, statistically placed along the chain:

$$(CFXO), (CF_2CF_2O), (CF_2CF_2CF_2O), (CF_2CF_2CF_2CF_2O),$$
$$(CR_4R_5CF_2CF_2O), (CF(CF_3)CF_2O), (CF_2CF(CF_3)O),$$

wherein

X=F, $CF_3$;

$R_4$ and $R_5$, equal to or different from each other, are selected from H, Cl, or perfluoroalkyl having from 1 to 4 carbon atoms.

In particular, the perfluoropolyether chain $R_f$ is selected from the following structures:

$$-(CF_2O)_a-(CF_2CF_2O)_b- \quad 1)$$

with b/a in the range 0.3–10, extremes included;

$$-(C_3F_6O)_r-(C_2F_4O)_b-(CFLO)_t- \quad 2)$$

with r/b=0.5–2 when b is different from 0,
(r+b)/t=10–30 when t is different from 0,
b and/or t can also be 0;
L is selected from F, $CF_3$;
a, b, r, t are integers the sum of which is such that Rf has values of number average molecular weight Mn as indicated above.
—$(C_3F_6O)$— can represent units of formula:

$$-(CF(CF_3)CF_2O)-$$

and/or $$-(CF_2-CF(CF_3)O)-;$$

The alcoholic precursors of formula (IA) and (IIA) are obtainable by well known processes of the prior art. To obtain the (per)fluoropolyethers see for example the following patents: U.S. Pat. Nos. 3,665,041, 2,242,218, 3,715,378, 5,714,637 and EP 239,123. The functionalized fluoropolyethers having an hydroxyl termination (IA) and (IIA) are obtained for example according to EP 148,482, U.S. Pat. No. 3,810,874.

The phosphatization reaction (step b) to obtain the compounds of formula (I) and (II) is carried out at temperatures in the range 20° C.–120° C., preferably 40° C.–100° C. In this temperature range the ratio between monoester groups and diester groups obtained by the invention process is independent of the temperature itself. The rate of addition of the phosphoric anhydride is regulated so as to maintain the reaction temperature within the above limits.

The compound obtained in the phosphatization step b) is subsequently hydrolyzed (step c) and the organic phase is separated. Generally the hydrolysis is carried ou by adding water, or a solution of diluted hydrochloric acid to the reaction admixture, or alternatively by adding the reaction admixture to the aqueous phase.

Optionally the organic phase is separated (step d) in case by a suitable solvent immiscible in water such for example methylene chloride, ethyl acetate and others known in the prior art.

The compound is then isolated (step e) from the organic phase for example by the evaporation technique of the solvent.

By the process of the present invention phosphoric esters of formula (I) and (II) are obtained having a molar ratio between the monoester groups [—P(O)(OH)$_2$] and diester groups [>P(O)(OH)] [>PO(OH)] predetermined in connection with the amount of water used in step a). Besides, it has been found that the in the process of the invention the variation of the average molecular weight of the starting alcohol does not affect the molar ratio obtained between monoester/diester groups.

The invention process leads to the obtainment of a hydrolytically stable compound. In fact, even carrying out the phosphatization reaction in the presence of water, a reaction conversion always higher than 98% is obtained.

The Applicant has surprisingly found that the use of the ethoxylated alcoholic precursors of formula (IA) and (IIA) gives the advantage to carry out the phosphatization reaction in the presence of water to obtain the desired ratios monoester/diester groups. Said result is surprising and unexpected since it was not expected this effect due to the presence of water on fluorinated products of perfluoropolyether type, which, as well known, are hydrophobic.

Tests carried out by the Applicant (see the comparative Examples) show that in the case of not ethoxylated alcoholic precursors (q=1, Z=—O, —S in formula IA and IIA), the reaction conversion is very low (lower than 10%), when the reaction is carried out in the presence of water. In absence of water the phosphatization reaction takes place with good yields, but it is not possible to control the final monoester/diester composition in the desired ratios.

The mixtures of phosphoric esters having a PFPE structure of formula (I) or (II) having a predetermined ratio of monoester/diester groups and complete absence of triester groups result new. In the case of phosphoric esters of formula (II) deriving from bifunctional alcohols, the molar ratio monoester/diester groups can range between 60/40 and 90/10. In the case of phosphoric esters of formula (I) deriving from monofunctional alcohols, the molar ratio monoester/diester groups can range between 70/30 and 85/15.

The mono/diester admixtures of the invention are obtainable with a predetermined ratio starting from the same precursor alcohol; or starting from alcohols having different molecular weight. The predetermined mono/diester ratio is in connection with the amount of water used in step a).

As said the admixtures of the invention combine good hydro- and oil-repellence properties.

Optionally the mixtures of phosphoric esters of formula (I) and (II) can be neutralized by bases to obtain the corresponding salts having formula:

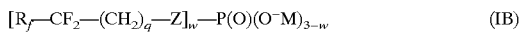

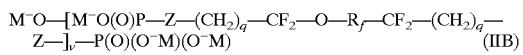

wherein M is equal to:

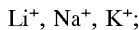

- $Li^+$, $Na^+$, $K^+$;
- $(NH_3R)^+$, wherein R=H or linear or branched $C_1$–$C_{22}$ alkyl radical, preferably H; R can optionally contain —OH groups; —$(NH_2RR')^+$, wherein R and R' are independently the one from the other linear or branched $C_1$–$C_{22}$ alkyl radicals; R and R' can optionally contain —OH groups or can be linked each other to form a cycle with the nitrogen atom, such as for example the morpholine group;
- $(NHRR'R'')^+$, wherein R, R'and R'' are independently the one from the other linear or branched $C_1$–$C_{22}$ alkyl radicals; R, R'and R'' can optionally contain —OH groups or can be linked each other to form a cycle with the nitrogen atom, such as for example the morpholine group.

As said, the salts of formula (IB) and (IIB) are obtained by neutralization of the esters of formula (I) and (II) with bases, such as for example alkaline metal hydroxides or secondary or tertiary amines. Preferred examples of bases are: potassium hydroxyde, sodium hydroxide, ammonium hydroxide, primary, secondary or tertiary amines such as for example methyl amine, diethyl amine, triethylamine, ethanolamine, diethanolamine, triethanolamine, morpholine and others.

The stoichiometry of the neutralization reaction can be controlled so as to reach only the first equivalence point, corresponding to the neutralization of the protons of the >P(O)(OH) groups and one of the two protons of the —P(O)(OH)$_2$ groups. The first acid proton of the phosphate to be neutralized is that of a strong acid and, as a result, a salt is obtained which in water produces a solution or dispersion having pH of about 7. For the neutralization of the second proton of the —P(O)(OH)$_2$ groups, it is instead necessary to reach a pH of about 10.

The phosphoric ester salts are particularly useful used in aqueous dispersions for the above mentioned hydro- and oil-repellence applications.

The present invention will be better illustrated from the following Examples, which have a merely indicative but not limitative purpose of the scope of the invention itself.

EXAMPLES

Example 1

(1% Moles H$_2$O)

100 g (0.138 equivalents) of a perfluoropolyoxyalkylene diol of general formula H(OCH$_2$CH$_2$)$_{1.6}$—O—CH$_2$—CF$_2$—O(CF$_2$CF$_2$O)$_b$—(CF$_2$O)$_a$—CF$_2$—O—(CH$_2$CH$_2$O)$_{1.6}$H having a number average molecular weight MW=1,440 and an average equivalent weight EW=724 are introduced into a 250 cc flask, equipped with magnetic stirrer. 0.025 g (0.001 moles, corresponding to 1% by moles of the equivalents of the diol) of demineralized water are added to the diol.

Then 9.9 g (0.069 moles) of P$_2$O$_5$ are added under stirring in a single portion. The temperature inside the reactor changes from 23° C. to 56° C. in about 45 minutes. The reaction mixture is then heated up to 100° C. and left under these conditions for about 8 hours.

After cooling 35 g of ethyl acetate and 120 g of demineralized water are then added and the reaction mixture is left under stirring at room temperature for about one hour. The phases are then let separate and the organic phase is stripped at 100° C./1 mmHg. 103.2 g of compound of formula:

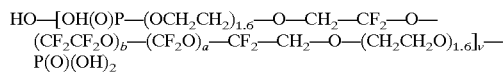

are thus obtained, wherein v=1–6 such that the average equivalent weight (EW) determined by chemical titration is 715.

By $^{31}$P-NMR analysis the molar ratio between monoester/diester groups is determined which results equal to 60/40. Furthermore a complete absence of triester groups is noticed.

The reaction conversion is determined by $^{13}$C-NMR analysis and it results to be higher than 98%. The yield of the isolated compound is 92.8%.

Example 2

(10% Moles H$_2$O)

Using the equipment of Example 1, 100 g (0.138 equivalents) of a perfluoropolyoxyalkylene diol of general formula H(OCH$_2$CH$_2$)$_{1.6}$—O—CH$_2$—CF$_2$—O(CF$_2$CF$_2$O)$_b$—(CF$_2$O)$_a$—CF$_2$—CH$_2$—O—(CH$_2$CH$_2$O)$_{1.6}$ H having a number average molecular weight MW=1,440 and an average equivalent weight EW=724 are introduced into the reactor. 0.24 g (0.0138 moles, corresponding to 10% of the equivalents of the diol) of demineralized water are added to the diol. Then 9.9 g (0.069 moles) of P$_2$O$_5$ are added under stirring in a single portion. The reaction and the isolation of the compound are carried out as in Example 1.

104.6 g of compound of formula:

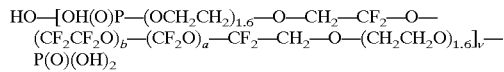

are thus obtained, wherein v=1–6 such that the average equivalent weight (EW) determined by chemical titration is 605.

By $^{31}$P-NMR analysis the molar ratio between monoester/diester groups is determined which results equal to 72/28. Furthermore a complete absence of triester groups is noticed.

The reaction conversion is determined by $^{13}$C-NMR analysis and it results to be higher than 98%. The yield of the isolated compound is 94%.

Example 3

(20% Moles H$_2$O)

Using the equipment of Example 1, 100 g (0.138 equivalents) of a perfluoropolyoxyalkylene diol of general formula H(OCH$_2$CH$_2$)$_{1.6}$—O—CH$_2$—CF$_2$—O(CF$_2$CF$_2$O)$_b$—(CF$_2$O)$_a$—CF$_2$—CH$_2$—O—(CH$_2$CH$_2$O)$_{1.6}$H having a number average molecular weight MW=1,440 and an average equivalent weight EW=724 are introduced into the reactor. 0.48 g (0.0276 moles, corresponding to 20% of the equivalents of thr diol) of demineralized water are added to the diol. Then 9.9 g (0.069 moles) of P$_2$O$_5$ are added under stirring in a single portion. The reaction and the isolation of the compound are carried out as in Example 1.

103.8 g of compound of formula:

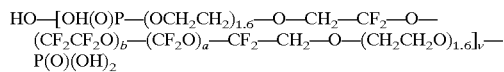

are thus obtained, wherein v=1–6 such that the average equivalent weight (EW) determined by chemical titration is 530.

By $^{31}$P-NMR analysis the molar ratio between monoester/diester groups is determined which results equal to 83/17. Furthermore a complete absence of triester groups is noticed.

The reaction conversion is determined by $^{13}$C-NMR analysis and it results to be higher than 98%. The yield of the isolated compound is 93.3%.

Example 4

(40% Moles $H_2O$)

Using the equipment of Example 1, 100 g (0.138 equivalents) of a perfluoropolyoxyalkylene diol of general formula $H(OCH_2CH_2)_{1.6}$—O—$CH_2$—$CF_2$—$O(CF_2CF_2O)_b$—$(CF_2O)_a$—$CF_2$—$CH_2$—O—$(CH_2CH_2O)_{1.6}H$ having a number average molecular weight MW=1,440 and an average equivalent weight EW=724 are introduced into the reactor. 0.98 g (0.055 moles, corresponding to 40% of the equivalents of the diol) of demineralized water are added to the diol. Then 9,9 g (0.069 moles) of $P_2O_5$ are added under stirring in a single portion. The reaction and the isolation of the compound are carried out as in Example 1. 102.4 g of compound of formula:

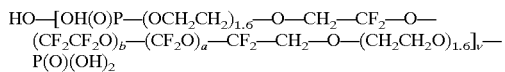

are thus obtained, wherein v=1–6 such that the average equivalent weight (EW) determined by chemical titration is 479.

By $^{31}$P-NMR analysis the molar ratio between monoester/diester groups is determined which results equal to 89/11. Furthermore a complete absence of triester groups is noticed.

The reaction conversion is determined by $^{13}$C-NMR analysis and it results to be higher than 98%. The yield of the isolated compound is 92%.

Example 5

(40% Moles $H_2O$)

Using the equipment of Example 1, 100 g (0.151 equivalents) of a perfluoropolyoxyalkylene diol of general formula $H(OCH_2CH_2)_{2.1}$—O—$CH_2$—$CF_2$—$O(CF_2CF_2O)_b$—$(CF_2O)_a$—$CF_2$—$CH_2$—O—$(CH_2CH_2O)_{2.1}H$ having a number average molecular weight MW=1,273 and an average equivalent weight EW=664 are introduced into the reactor. 1.08 g (0.060 moles, corresponding to 40% of the equivalents of the diol) of demineralized water are added to the diol. Then 10.7 g (0.075 moles) of $P_2O_5$ are added under stirring in a single portion. The reaction and the isolation of the compound are carried out as in Example 1. 100.7 g of compound of formula:

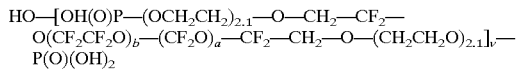

are thus obtained, wherein v=1–6 such that the average equivalent weight (EW) determined by chemical titration is 435.

By $^{31}$P-NMR analysis the molar ratio between monoester/diester groups is determined which results equal to 89/11. Furthermore a complete absence of triester groups is noticed.

The reaction conversion is determined by $^{13}$C-NMR analysis and it results to be higher than 98%. The yield of the isolated compound is 93%.

This Example shows that, the reaction conditions being equal, the variation of the average molecular weight of the starting alcohol does not affect the molar ratio obtained between monoester/diester groups.

Example 6

(40% Moles $H_2O$)

Using the equipment of Example 1, 100 g (0.123 equivalents) of a perfluoropolyoxyalkylene diol of general formula $H(OCH_2CH_2)_{1.4}$—O—$CH_2$—$CF_2$—$O(CF_2CF_2O)_b$—$(CF_2O)_a$—$CF_2$—$CH_2$—O—$(CH_2CH_2O)_{1.4}H$ having a number average molecular weight MW=1,570 and an average equivalent weight EW=811 are introduced into the reactor. 0.88 g (0.049 moles, corresponding to 40% of the equivalents of the diol) of demineralized water are added to the diol. Then 8.7 g (0.061 moles) of $P_2O_5$ are added under stirring in a single portion. The reaction and the isolation of the compound are carried out as in Example 1. 105.9 g of compound of formula:

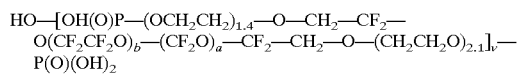

are thus obtained, wherein v=1–6 such that the average equivalent weight (EW) determined by chemical titration is 526.

By $^{31}$P-NMR analysis the molar ratio between monoester/diester groups is determined which results equal to 89/11. Furthermore a complete absence of triester groups is noticed.

The reaction conversion is determined by $^{13}$C-NMR analysis and it results to be higher than 98%. The yield of the isolated compound is 96%.

This Example shows that, the reaction conditions being equal, the variation of the average molecular weight of the starting alcohol does not affect the molar ratio obtained between monoester/diester groups.

Example 7

(Comparative)

(10% Moles $H_2O$)

Using the equipment of Example 1, 100 g (0.195 equivalents) of a perfluoropolyoxyalkylene diol of general formula

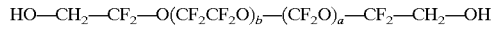

having a number average molecular weight MW=987 and an average equivalent weight EW=513 are introduced into the reactor. 0.35 g (0.0195 moles, corresponding to 10% of the equivalents of the diol) of demineralized water are added to the diol. Then 13.8 g (0.097 moles) of $P_2O_5$ are added under stirring in a single portion. The reaction is carried out as in Example 1. The reaction mixture appears unhomogeneous during the whole experiment. The NMR analysis of the reaction compound shows a low conversion, lower than 10%, of the alcohol to the phosphate.

This Example shows that in the case of non ethoxylated alcoholic precursors, the phosphatization reaction carried out in the presence of water takes place only in a minimum part.

Example 8

(Comparative)

(40% Moles $H_2O$)

Using the equipment of Example 1, 100 g (0.195 equivalents) of a perfluoropolyoxyalkylene diol of general formula

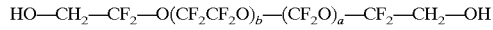

having a number average molecular weight MW=987 and an average equivalent weight EW=513 are introduced into the reactor. 1.4 g (0.078 moles, corresponding to 40% of the equivalents of the diol) of demineralized water are added to the diol. Then 13.8 g (0.097 moles) of $P_2O_5$ are added under stirring in a single portion. The reaction is carried out as in Example 1. The reaction mixture appears unhomogeneous during the whole experiment. The NMR analysis of the reaction compound shows a low conversion, lower than 10%, of the alcohol to the phosphate.

This Example shows that in the case of non ethoxylated alcoholic precursors, the phosphatization reaction carried out in the presence of water takes place only in a minimum part.

Example 9

(1% Moles $H_2O$)

100 g (0.16 equivalents) of a monofunctional perfluoropolyoxyalkylene alcohol of general formula

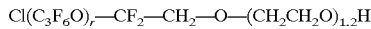

having a number average molecular weight MW=623 are introduced into a 250 cc flask, equipped with magnetic stirrer. 0.029 g (0.0016 moles, corresponding to 1% mole of the equivalents of the diol) of demineralized water are added to the diol. Then 11.4 g (0.08 moles) of $P_2O_5$ are added under stirring in a single portion. The temperature inside the reactor changes from 25° C. to 63° C. in about 45 minutes. The reaction mixture is then heated up to 100° C. and left under these conditions for about 8 hours.

After cooling 40 g of ethyl acetate and 120 g of demineralized water are then added and the reaction mixture is left under stirring at room temperature for about one hour. The phases are then let separate and the organic phase is stripped at 100° C./1 mmHg. 104.1 g of compound of formula:

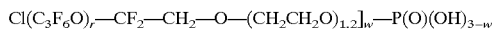

are thus obtained, wherein w=1–2 such that the average equivalent weight (EW) determined by chemical titration is 520.

By $^{31}$P-NMR analysis the molar ratio between monoester/diester groups is determined which results equal to 70/30. Furthermore a complete absence of triester groups is noticed.

The reaction conversion is determined by $^{13}$C-NMR analysis and it results to be higher than 98%. The yield of the isolated compound is 93.1%.

Example 10

(10% Moles $H_2O$)

100 g (0.16 equivalents) of a monofunctional perfluoropolyoxyalkylene alcohol of general formula

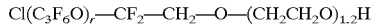

having a number average molecular weight MW=623 are introduced into a 250 cc flask, equipped with magnetic stirrer. 0.29 g (0.016 moles, corresponding to 10% of the equivalents of the alcohol) of demineralized water are added to the alcohol. Then 11.4 g (0.08 moles) of $P_2O_5$ are added under stirring in a single portion. The temperature inside the reactor changes from 25° C. to 67° C. in about 45 minutes. The reaction mixture is then heated up to 100° C. and left under these conditions for about 8 hours.

After cooling 40 g of ethyl acetate and 120 g of demineralized water are then added and the reaction mixture is left under stirring at room temperature for about one hour. The phases are then let separate and the organic phase is stripped at 100° C./1 mmHg. 106.4 g of product of formula:

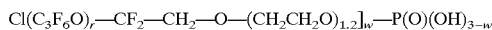

are thus obtained, wherein w=1–2 such that the average equivalent weight (EW) determined by chemical titration is 478.

By $^{31}$P-NMR analysis the molar ratio between monoester/diester groups is determined which results equal to 77/23. Furthermore a complete absence of triester groups is noticed.

The reaction conversion is determined by $^{13}$C-NMR analysis and it results to be higher than 98%. The yield of the isolated compound is 95%.

Example 11

(20% Moles $H_2O$)

100 g (0.16 equivalents) of a monofunctional perfluoropolyoxyalkylene alcohol of general formula

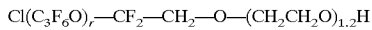

having a number average molecular weight MW=623 are introduced into a 250 cc flask, equipped with magnetic stirrer. 0.58 g (0.032 moles, corresponding to 20% of the equivalents of the alcohol) of demineralized water are added to the alcohol. Then 11.4 g (0.08 moles) of $P_2O_5$ are added under stirring in a single portion. The temperature inside the reactor changes from 25° C. to 69° C. in about 45 minutes. The reaction mixture is then heated up to 100° C. and left under these conditions for about 8 hours.

After cooling 40 g of ethyl acetate and 120 g of demineralized water are then added and the reaction mixture is left under stirring at room temperature for about one hour. The phases are then let separate and the organic phase is stripped at 100° C./1 mmHg. 106.1 g of compound of formula:

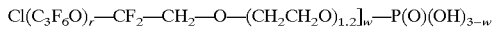

are thus obtained, wherein w=1–2 such that the average equivalent weight (EW) determined by chemical titration is 460.

By $^{31}$P-NMR analysis the molar ratio between monoester/diester groups is determined which results equal to 80/20. Furthermore a complete absence of triester groups is noticed.

The reaction conversion is determined by $^{13}$C-NMR analysis and it results to be higher than 98%. The yield of the isolated compound is 94.6%.

Example 12

(40% Moles $H_2O$)

100 g (0.16 equivalents) of a monofunctional perfluoropolyoxyalkylene alcohol of general formula

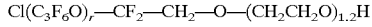

having a number average molecular weight MW=623 are introduced into a 250 cc flask, equipped with magnetic stirrer. 1.15 g (0.064 moles, corresponding to 40% of the equivalents of the alcohol) of demineralized water are added to the alcohol. Then 11.4 g (0.08 moles) of $P_2O_5$ are added under stirring in a single portion. The temperature inside the reactor changes from 25° C. to 75° C. in about 45 minutes. The reaction mixture is then heated up to 100° C. and left under these conditions for about 8 hours.

After cooling 40 g of ethyl acetate and 120 g of demineralized water are then added and the reaction mixture is left under stirring at room temperature for about one hour. The phases are then let separate and the organic phase is stripped at 100° C./1 mmHg. 107.5 g of product of formula:

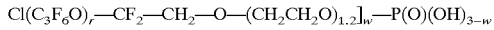

are thus obtained, wherein w=1–2 such that the average equivalent weight (EW) determined by chemical titration is 431.

By $^{31}$P-NMR analysis the molar ratio between monoester/diester groups is determined which results equal to 85/15. Furthermore a complete absence of triester groups is noticed.

The reaction conversion is determined by $^{13}$C-NMR analysis and it results to be higher than 98%. The yield of the isolated compound is 95.7%.

Example 13
(Comparative)
(10% Moles H$_2$O)

100 g (0.17 equivalents) of a monofunctional perfluoropolyoxyalkylene alcohol of general formula

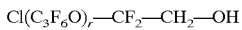

having a number average molecular weight MW=585 are introduced into a 250 cc flask, equipped with magnetic stirrer. 0.31 g (0.017 moles, corresponding to 10% of the equivalents of the alcohol) of demineralized water are added to the alcohol. Then 12.1 g (0.085 moles) of P$_2$O$_5$ are added under stirring in a single portion. The reaction mixture is then heated up to 100° C. and left under these conditions for about 8 hours. The reaction mixture appears unhomogeneous during the whole experiment.

The NMR analysis of the reaction compound shows a low conversion, lower than 10%, of the alcohol to phosphate.

This Example shows that in the case of non ethoxylated alcoholic precursors, the phosphatization reaction carried out in the presence of water takes place only in a minimum part.

Example 14
(Comparative)
(40% Moles H$_2$O)

100 g (0.17 equivalents) of a monofunctional perfluoropolyoxyalkylene alcohol of general formula

having a number average molecular weight MW=585 are introduced into a 250 cc flask, equipped with magnetic stirrer. 1.2 g (0.068 moles, corresponding to 40% of the equivalents of the alcohol) of demineralized water are added to the alcohol. Then 12.1 g (0.085 moles) of P$_2$O$_5$ are added under stirring in a single portion. The reaction mixture is then heated up to 100° C. and left under these conditions for about 8 hours.

The reaction mixture appears unhomogeneous during the whole experiment.

The NMR analysis of the reaction compound shows a low conversion, lower than 10%, of the alcohol to phosphate.

This Example shows that in the case of non ethoxylated alcoholic precursors, the phosphatization reaction carried out in the presence of water takes place only in a minimum part.

What is claimed is:

1. A process to obtain phosphoric mono- and diester mixtures having the formula:

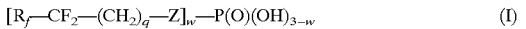
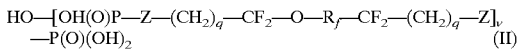

wherein:
w=1–2;
v=1–6,
q=an integer from 1 to 20,
Z=O(C$_2$H$_4$O)$_p$—, O(CH$_2$)$_n$—O—, O(C$_3$H$_6$O)$_p$— or S(C$_2$H$_4$O)$_p$—,
S(C$_3$H$_6$O)$_p$—;
n=an integer from 1 to 20;
p=an integer from 1 to 5

R$_f$ in formula (II) represents a (per)fluoropolyether chain;

R$_f$ in formula (I) is a monofunctional perfluoropolyether chain wherein the chain end group is selected from:

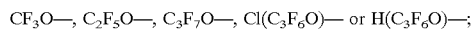

said process comprising the following steps:
a) a monofunctional alcohol having a perfluoropolyoxyalkylene structure of formula:

 (IA)

or a α,ω-diol having a perfluoropolyoxyalkylene structure of formula:

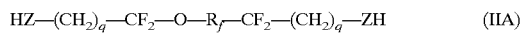 (IIA)

wherein R$_f$, Z and q have the above meanings, is added with an amount of water in the range 1–60% by moles, with respect to the alcohol equivalents;

b) the admixture obtained in step a) is reacted with phosphoric anhydride, P$_2$O$_5$, added in a single portion or in more portions with a ratio between the alcohol equivalents and the moles of phosphoric anhydride in the range 1.5:1–4:1;

c) the compound obtained in step b) is hydrolysed by water or by a diluted solution of hydrochloric acid;

d) optionally the organic phase is separated by a solvent immiscible in water and e) the product is recovered from the organic phase.

2. A process according to claim 1, wherein the perfluoropolyether chain R$_f$ has a number average molecular weight in the range 300–8,000 and comprises repeating units, statistically placed along the chain, having at least one of the following structures:

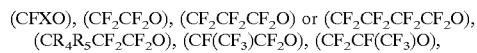

wherein
X=F, CF$_3$;
R$_4$ and R$_5$, equal to or different from each other, are selected from H, Cl, or perfluoroalkyl having from 1 to 4 carbon atoms.

3. A process according to claim 2, wherein R$_f$ is selected from the following structures:

 1)

with b/a in the range 0.3–10 or;

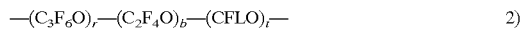 2)

with r/b=0.5–2 when b is different from 0,
(r+b)/t=10–30 when t is different from 0,
b and/or t can also be 0;
L is selected from F and CF$_3$;
a, b, r, t are integers the sum of which is such that Rf has the values of number average molecular weight as found in claim 2.

4. A process according to claim 1, wherein the phophatization reaction (step b) is carried out at temperatures in the range 20° C.–120° C.

5. A process according to claim 1, wherein the hydrolysis (step c) is carried out by adding water, or a solution of diluted hydrochloric acid to the reaction admixture, or alternatively by adding the reaction admixture to the aqueous phase.

6. A process according to claim 1, wherein the organic phase is separated (step d) by a suitable solvent immiscible in water selected from methylene chloride or ethyl acetate.

7. A process according to claim 1, wherein the compound is isolated (step e) from the organic phase by the evaporation technique of the solvent.

8. A process according to claim 1, comprising furthermore the neutralization by bases of the phosphoric esters of formula (I) and (II) to obtain the corresponding salts.

* * * * *